US00PP24514P2

(12) United States Plant Patent
Werner et al.

(10) Patent No.: US PP24,514 P2
(45) Date of Patent: Jun. 3, 2014

(54) ***BUDDLEJA* PLANT NAMED 'PURPLE HAZE'**

(50) Latin Name: ***Buddleja*. complex hybrid including *davidii, lindleyana,* and *globasa***
Varietal Denomination: Purple Haze

(75) Inventors: Dennis James Werner, Raleigh, NC (US); Layne Karlton Snelling, Cary, NC (US)

(73) Assignee: North Carolina State University, Raleigh, NC (US)

( * ) Notice: Subject to any disclaimer, the term of this patent is extended or adjusted under 35 U.S.C. 154(b) by 479 days.

(21) Appl. No.: 12/931,038

(22) Filed: Jan. 24, 2011

(51) Int. Cl.
*A01H 5/00* (2006.01)

(52) U.S. Cl.
USPC ..... Plt./242

(58) Field of Classification Search
USPC ..... Plt./242
See application file for complete search history.

(56) References Cited

U.S. PATENT DOCUMENTS

| | | | | |
|---|---|---|---|---|
| PP19,950 | P3 * | 4/2009 | Werner et al. | Plt./242 |
| PP22,080 | P2 * | 8/2011 | Podaras | Plt./242 |
| PP22,109 | P2 * | 9/2011 | Podaras | Plt./242 |
| PP22,143 | P2 * | 9/2011 | Podaras | Plt./242 |
| PP23,464 | P2 * | 3/2013 | Valin | Plt./242 |

OTHER PUBLICATIONS

Werner, Dennis J. and Layne K. Snelling. "'Purple Haze', 'Miss Molly', and 'Ice Chip' *Buddleja*" HortScience 46(9): 1330-1332, 2011.*

* cited by examiner

*Primary Examiner* — Wendy C Haas

(57) ABSTRACT

*Buddleja* 'Purple Haze' is a new and distinct variety of butterfly bush that has the following unique combination of desirable features that are outstanding in a new variety.

1. Moderate vigor resulting in compact growth habit.
2. Ease of asexual propagation using softwood or semi-hardwood cuttings.
3. Spreading growth habit with multi-branched arching stems.
4. Unique pendant panicles with purple-violet flowers.
5. Female sterility and reduced seed set, resulting in less opportunity for seedlings to originate in the landscape setting.

5 Drawing Sheets

Latin name of the genus and species: Genus: *Buddleja*. Species: complex hybrid including *davidii, lindleyana,* and *globosa*.

Variety denomination: The inventive cultivar of *Buddleja* disclosed herein has been given the variety denomination 'Purple Haze'.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventors in Raleigh, N.C., United States. One of the objectives of the breeding program was to develop a semi-compact, spreading *Buddleja* with pendant flowers. 'Purple Haze' was selected in Jackson Springs, N.C. in 2005 from a population of 231 seedling progeny derived from a hand pollinated cross of 'Miss Ruby'×('Honeycomb×('Nanho Purple'×*Buddleja lindleyana*)) made in 2004 in Raleigh, N.C. 'Miss Ruby' (U.S. Plant Pat. No. 19,950) was released in 2008. It is described as a compact upright plant with bright pink flowers. 'Honeycomb' (unpatented) was released in 1997, and is described as a hybrid of *Buddleja davidii* and *Buddleja globosa*. 'Nanho Purple' (unpatented) is a semi-compact selection of *Buddleja*

*davidii* var. *nanhoensis*. *Buddleja lindleyana* is a species native to China, but used in garden settings. All four parents are available in commerce.

The seeds resulting from the 2004 controlled hybridization process were harvested in fall of 2004 and germinated in Raleigh, N.C. in the winter of 2005. The resulting 231 seedlings were planted in field trials in spring of 2005 at Jackson Springs, N.C. These plants flowered in summer 2005, and one plant, designated NC2005-29, was selected for its compact growth habit, mounding and spreading habit, large attractive purple-violet flowers, pendant flower panicles, and lack of seed set (female sterile). This original plant demonstrated characteristics identical to those subsequently expressed on other plants when propagated from stem cuttings. This single plant is the subject of the present invention *Buddleja* 'Purple Haze'.

The distinguishing traits of 'Purple Haze' are semi-compact growth habit, mounding spreading growth, gray-green leaf color, large purple-violet flowers that are arranged in arching panicles, and female sterility. The cultural requirements for 'Purple Haze' are well-drained soil, full sun, and moderate moisture. 'Purple Haze' exhibits no serious pest or disease problems known to the inventors, except for occasional spider mite infestation during periods of hot, dry weather.

The closest comparison known to the inventors is the species *Buddleja lindleyana* (no named cultivars in commerce). Plants and flowers of this new variety differ from *Buddleja*

*lindleyana*. In direct comparisons of 'Purple Haze' and *Buddleja lindleyana* in the inventor's experimental trials, plants of 'Purple Haze' are consistently more compact, more highly branched, more dense, have larger flower panicles, and produce less viable seed than *Buddleja lindleyana*. 'Purple Haze' is distinctly different from its female parent, 'Miss Ruby'. 'Miss Ruby' has upright growth and is considerable taller than 'Purple Haze'. After two growing seasons, average height in replicated trials was 72 and 106 cm for unpruned plants of 'Purple Haze' and 'Miss Ruby', respectively.

The first asexual propagation of 'Purple Haze' was conducted by the inventors in fall 2005 in Raleigh, N.C., and 'Purple Haze' has subsequently been propagated in the same location in years 2006 and 2007. In all cases, the original plant selection was propagated asexually by softwood to semi-hardwood stem cuttings. Such cuttings root readily under mist in about 14 to 21 days, and resume normal growth. Fifteen plants derived from stem cuttings of the variety were established in test plots in Jackson Springs, N.C. and two plants were established in Raleigh, N.C. in 2007. During all asexual propagation, the characteristics of the original plant have been maintained. Plants derived from stem cuttings exhibit characteristics identical to those of the original plant, and no aberrant phenotypes have appeared.

Test plantings and performance evaluation over five years at Jackson Springs and Raleigh, N.C. demonstrate this variety to be relatively consistent in its characteristics even under the different growing conditions associated with yearly climatic variation.

Plants of the new variety are moderately vigorous after establishment in the field, being less vigorous and more compact than most cultivars of butterfly bush. Young plants have averaged about 0.4 meters of growth per year. Plants are spreading and mounding in growth habit. Flowering occurs in the first year of growth on newly formed wood. The inflorescence is an arching panicle, and shows a purple-violet flower color. Flowering usually begins in early June in Jackson Springs, N.C., and continues throughout the growing season until the first freeze event in October or November. An individual inflorescence flowers for about 10-14 days, depending on temperature, but new flowers are made during the entire growing season. Female fertility of flowers is very low, and the new cultivar sets virtually no seed in a field or landscape setting, an asset in landscape plantings.

'Purple Haze' is distinguished from other related known cultivars based on the unique combination of traits including compact habit, spreading mounding growth, pendant purple-violet flowers, and female sterility.

The new variety has been named the 'PURPLE HAZE' cultivar. First public offer for sale of 'Purple Haze' was made by Spring Meadow Nursery, Grand Haven, Mich., U.S.A. on Aug. 1, 2010, but no sale of plants has yet taken place at the time of application.

SUMMARY OF THE INVENTION

'Purple Haze' is a new and distinct variety of butterfly bush that has the following unique combination of desirable features outstanding in a new variety. In combination these traits set 'Purple Haze' apart from all other existing varieties of butterfly bush known to the inventors.

1. 'PURPLE HAZE' has low to moderate vigor resulting in compact growth habit.
2. 'PURPLE HAZE' is asexually propagated using softwood or semi-hardwood cuttings.
3. 'PURPLE HAZE' demonstrates spreading growth habit and arching, multi-branched stems and flower panicles.
4. 'PURPLE HAZE' exhibits very low female fertility and reduced seed set, resulting in less opportunity for seedlings to originate in the landscape setting.
5. 'PURPLE HAZE' has purple-violet flower color.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'Purple Haze'. Photographs were taken from two to four-year-old plants growing in Raleigh, N.C. and Jackson Springs, N.C.

DETAILED BOTANICAL DESCRIPTION OF THE VARIETY

Figure 1:
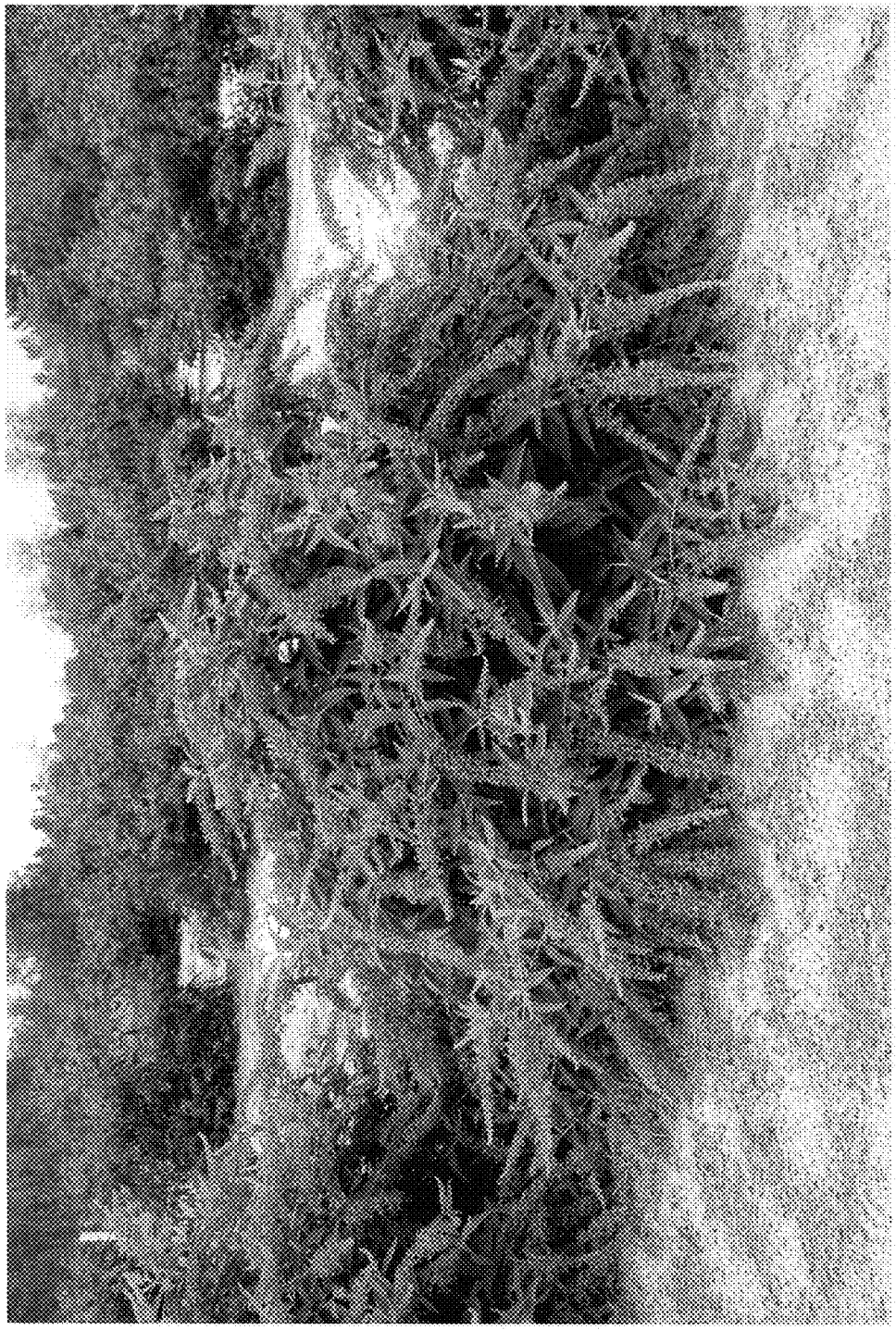
FIG. 1 shows a typical plant of 'PURPLE HAZE', showing the compact growth, arching branches, and pendant purple-violet flowers.
Figure 2:
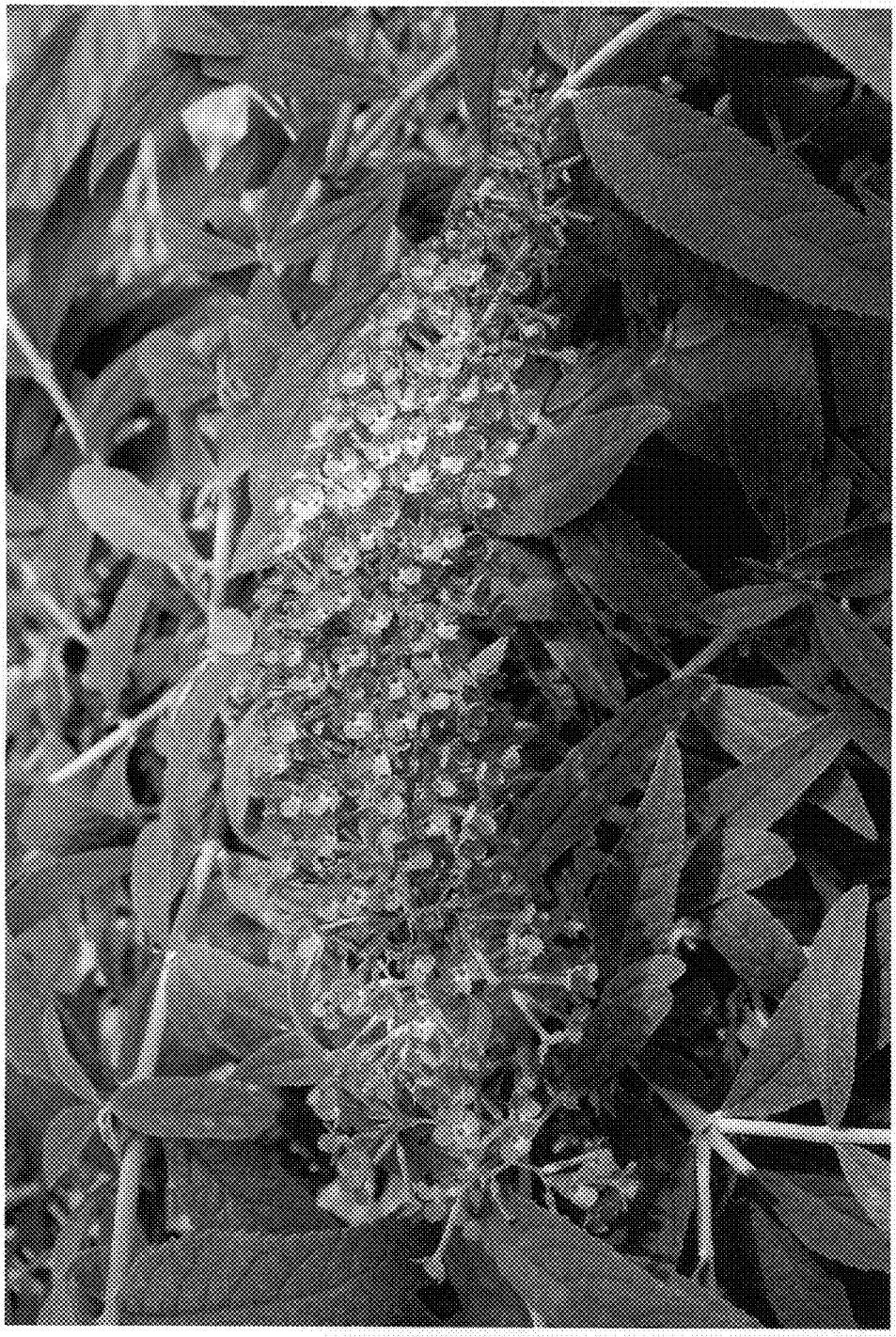
FIG. 2 shows the entire inflorescence of 'PURPLE HAZE.
Figure 3:
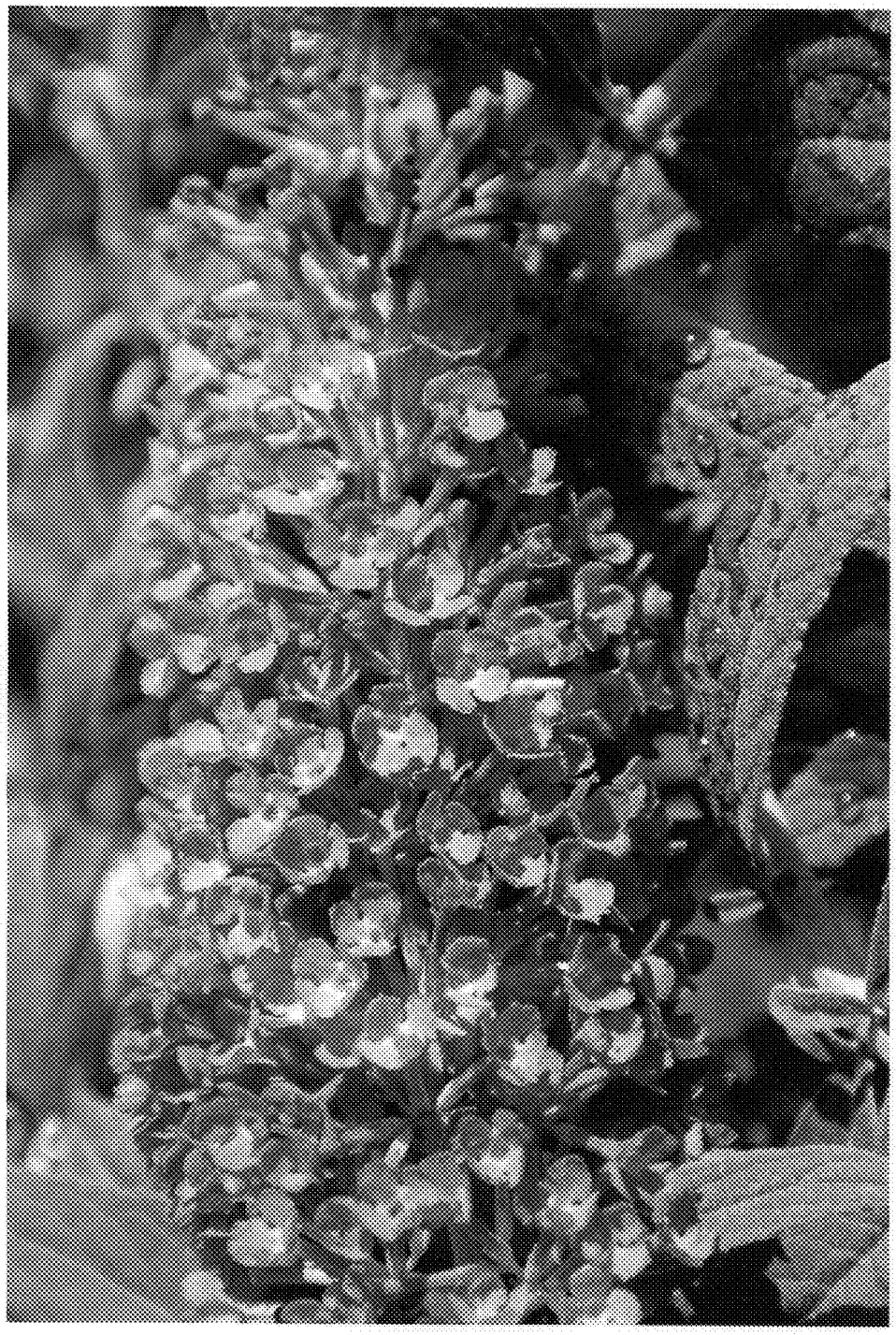
FIG. 3 shows a close-up view of the inflorescence of 'PURPLE HAZE', showing the violet-purple color of the individual flowers in the inflorescence.
Figure 4:
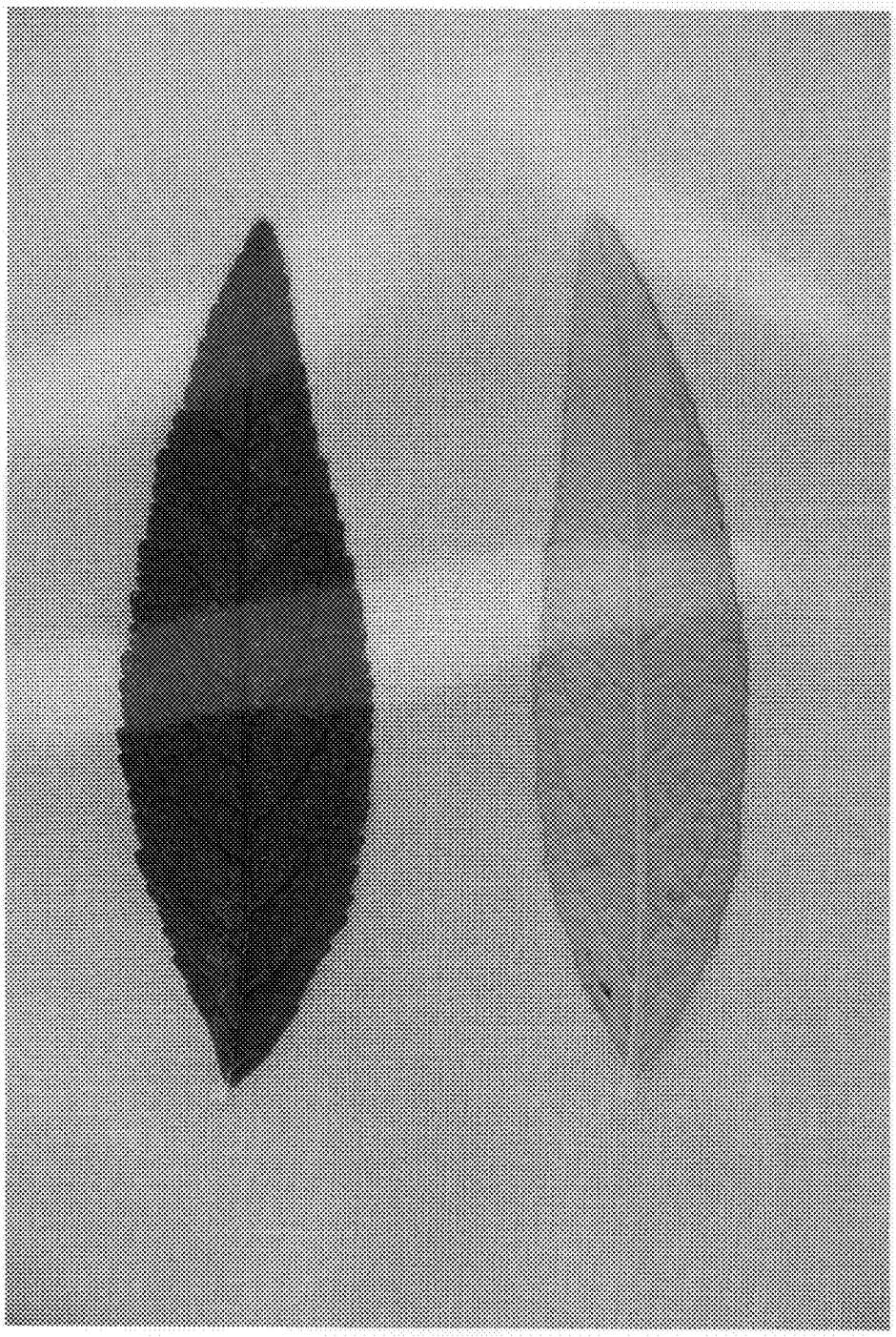
FIG. 4 shows the typical coloration and form of leaves of 'PURPLE HAZE'. This figure shows the upper (top) and lower (bottom) leaf surface.
Figure 5:
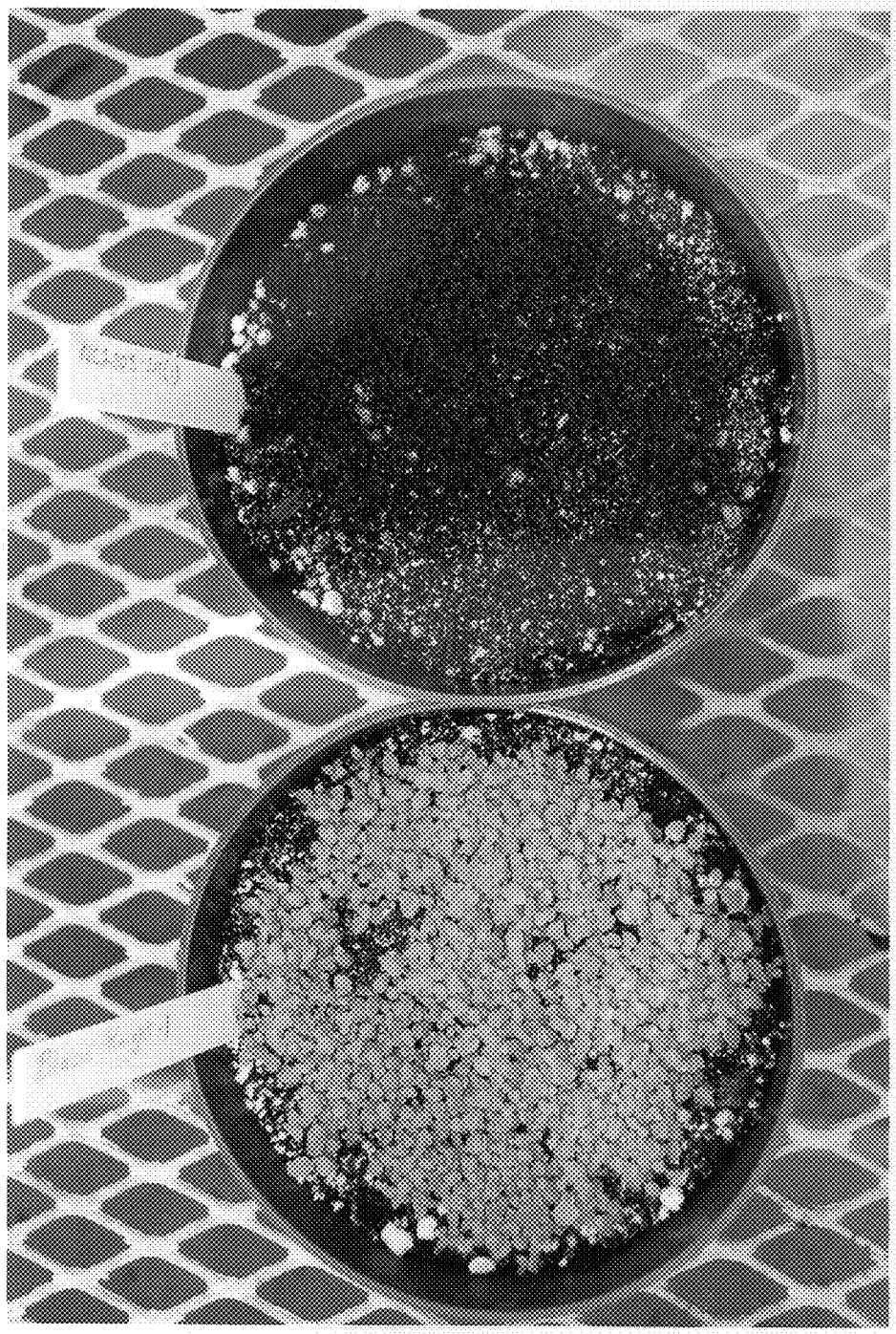
FIG. 5 shows lack of seed germination (right pot) from 'Purple Haze' (5 entire flower panicles crushed and sown) as compared to the high numbers of seedlings derived from only a small subset of seed pods on one flower panicle of commercial unpatented cultivar 'Black Knight' (left pot).

The following is a detailed description of the botanical and ornamental characteristics of the subject butterfly bush 'PURPLE HAZE'. Color data are based on *The Royal Horticultural Society Colour Chart*, The Royal Horticultural Society, London, 2007 edition. Where dimensions, sizes, colors and other characteristics are given, it is to be understood that such characteristics are approximations of averages set forth as accurately as practicable.

The descriptions reported herein are from four-year-old specimens grown out-of-doors in Jackson Springs, N.C.

Genus: *Buddleja.*

Species: Complex hybrid, including *davidii, globosa*, and *lindleyana.*

Denomination: 'PURPLE HAZE'.

Commercial classification: Shrub, deciduous.

Common name: Butterfly bush.

Type: Ornamental.

Uses: Patio container plant, herbaceous perennial border, or shrub border for residential and commercial landscapes.

Cultural requirements: Full sun exposure, well-drained soil, and moderate moisture.

Parentage: 'PURPLE HAZE' is a third-generation hybrid that resulted from the original cross pollination of the following *Buddleja* parents: Seed parent='Miss Ruby'. Pollen parent=hybrid of 'Honeycomb'×('Nanho Purple'× *Buddleja lindleyana*).

Plant description:

*Blooming period.*—June through October.

*Blooming habit.*—Paniculate.

*Vigor.*—Low to moderate vigor.

*Plant habit*.—Compact, spreading habit.
*Height and spread*.—1.17 m (height) and 1.63 m (width).
*Hardiness*.—To date, hardy to minus 8 degrees Centigrade. Not tested below this temperature. Anticipated adapted from USDA hardiness zones 5-9.
*Propagation*.—Softwood to semi-hardwood cuttings under intermittent mist. Roots typically form in 2-3 weeks.
*Root system*.—Fibrous, spreading.
*Seasonal interest*.—Purple-violet arching flowers in spring, summer, and fall on a compact shrub.
*Disease and pest susceptibility and resistance*.—No particular susceptibility or resistance, except occasionally susceptible to spider mites under very hot and dry conditions.
*Special growing requirements*.—Moderate yearly pruning in late winter or early spring prior to bud break is recommended to encourage more profuse flowering.

Stems:
*Shape*.—Stem cross section is quadrangular.
*Length*.—Average 55 cm.
*Color*.—Yellow-green (RHS 145C) on recently formed shoots.
*Diameter*.—5 mm at base of new growth.
*Stem surface*.—Pubescent.
*Pubescence*.—Sparse.
*Internode length*.—3.8 cm in the middle of new growth.

Foliage:
*Type*.—Deciduous.
*Leaf arrangement*.—Opposite, decussate.
*Leaf division*.—Simple.
*Leaf shape*.—Elliptic.
*Leaf base*.—Attenuate.
*Leaf apex*.—Acuminate.
*Leaf venation*.—Pinnate.
*Leaf surface* (*abaxial*).—Glaucous.
*Leaf margin*.—Serrulate.
*Leaf attachment*.—Petiolate.
*Petiole dimensions*.—5.2 mm length. 1.0 mm width.
*Petiole shape*.—Sulcate and pubescent.
*Petiole color*.—RHS 145C.
*Leaf color*.—Adaxial side=green (RHS 137B). Abaxial side=grayed-green (RHS 194D).
*Leaf length*.—Average length (5 leaves)=10.4 cm.
*Leaf width*.—Average width (5 leaves)=2.6 cm.
*Foliar fragrance*.—None detectable.

Flowers:
*Inflorescence*.—Loose panicle.
*Petals*.—4 in number.
*Fused or unfused*.—Fused at base.
*Petal margin*.—Entire.
*Petal apex*.—Rounded lobes, serrulate.
*Petal base*.—Truncate.
*Petal surfaces*.—Glaucous.
*Petal shape*.—Rotund.
*Petal dimensions*.—15 mm length. 5.4 mm width.
*Petal color*.—Adaxial and abaxial surface=Purple violet (RHS N82A).
*Flower shape*.—Salverform.
*Corolla tube color*.—Purple with orange undertones.
*Corolla tube surfaces* (*inner and outer surfaces*).—Pubescent.
*Corolla tube shape*.—Tubular.
*Color of peduncle*.—Grayed-green (RHS 193A).
*Peduncle surface*.—Glaucous.
*Peduncle length*.—3.4 cm.
*Peduncle shape*.—Flattened oval in cross section.
*Pedicel dimensions*.—1.0 mm in length and less than 1 mm in diameter.
*Pedicel color*.—Grayed-green (RHS 194A).
*Pedicel shape*.—Flattened oval in cross section.
*Pedicel surface*.—Glaucous.
*Flowers persistent or self-cleaning*.—Flowers are persistent.
*Lastingness of the overall inflorescence*.—1-2 weeks.
*Lastingness of an individual flower*.—3-5 days.
*Dimensions of inflorescence*.—19.6 cm length. 5.7 cm width.
*Dimensions of entire individual flower*.—15 mm length. Diameter 5.4 mm at apex tapering to 1 mm. at base.
*Quantity of flowers*.—85 flowers per panicle (average of 5 panicles).
*Bud color*.—Violet-blue (RHS 90A).
*Bud apex*.—Rounded lobes, serrulate.
*Bud surface*.—Glaucous.
*Bud shape*.—Elongated, linear balloon.
*Calyx shape*.—Tubular.
*Calyx dimensions*.—2.0 mm in width and 4.0 mm in length.
*Sepals*.—Four in number.
*Sepal shape*.—Lanceolate.
*Sepal apex*.—Acute.
*Sepal margin*.—Entire.
*Sepal surface*.—Glabrous.
*Sepal color*.—Grayed-green (RHS193A).
*Flower fragrance*.—Distinct sweet fragrance.

Reproductive organs:
*Stamens*.—Four, fused to inside of petals.
*Anther shape*.—Oblong.
*Anther dimensions*.—1 mm in length and <1 mm wide.
*Filament size*.—No filament.
*Filament color*.—No filament.
*Pollen amount*.—Moderate.
*Pollen color*.—RHS 11D (yellow).
*Pistil*.—One in number.
*Pistil dimensions*.—4 mm in length, and less than 1 mm in diameter.
*Stigma color*.—Yellow-green (RHS 144C).
*Ovary*.—Present.
*Ovary position*.—Superior.
*Ovary shape*.—Oval.
*Fertility*.—Low to no seed set in a field setting.

Fruit:
*Type*.—Swelled capsule. Rarely observed.
*Dimensions*.—3.0 mm. in length (variable) and 1.6 mm. in diameter (variable).
*Color*.—Yellow-green (RHS 144C) when immature.

Herbarium voucher: A voucher of 'Purple Haze' will be deposited into the Herbarium of North Carolina State University (NCSU) in Raleigh, N.C., USA upon patenting.

That which is claimed is:

1. A new and distinct variety of butterfly bush (*Buddleja*) substantially as illustrated and described, characterized by its compact growth habit, arching stems, pendant panicles, purple-violet flower color, and female sterility.

* * * * *